United States Patent
Shoher et al.

(10) Patent No.: US 6,506,054 B2
(45) Date of Patent: Jan. 14, 2003

(54) METHOD OF FORMING A DENTAL COPING

(76) Inventors: Itzhak Shoher, P.O. Box 58069, Tel Aviv (IL); Aharon E. Whiteman, P.O. Box 58069, Tel Aviv (IL)

( * ) Notice: Subject to any disclaimer, the term of this patent is extended or adjusted under 35 U.S.C. 154(b) by 23 days.

(21) Appl. No.: 09/811,453

(22) Filed: Mar. 20, 2001

(65) Prior Publication Data

US 2002/0137011 A1 Sep. 26, 2002

(51) Int. Cl.⁷ ................................................. A61C 5/10
(52) U.S. Cl. ........................... 433/223; 433/215; 264/19
(58) Field of Search .................................. 433/215, 223, 433/228.1; 264/19

(56) References Cited

U.S. PATENT DOCUMENTS

| | | | | |
|---|---|---|---|---|
| 4,937,928 A | * | 7/1990 | van der Zel | 433/223 |
| 5,347,454 A | * | 9/1994 | Mushabac | 364/413.28 |
| 5,565,152 A | * | 10/1996 | Oden et al. | 264/19 |
| 5,730,600 A | * | 3/1998 | Shoher et al. | 433/223 |
| 5,938,446 A | * | 8/1999 | Andersson et al. | 433/223 |
| 6,287,121 B1 | * | 9/2001 | Guiot et al. | 433/223 |
| 6,354,836 B1 | * | 3/2002 | Panzera et al. | 433/215 |

* cited by examiner

Primary Examiner—John J. Wilson

(57) ABSTRACT

An automated method for forming a dental coping which comprises: scanning a three dimensional image of the die of the tooth or teeth to be restored; digitizing the scanned three dimensional image into digital information, storing the digital information in a computer; feeding the digital information from the computer into a computerized numerical control cutting machine; cutting out a section of material of metallic composition into a two dimensional configuration representing a two dimensional lay out of the scanned three dimensional image, adapting the cut out section of material over the die so that the material covers the die surface in close engagement therewith to form a single three dimensional structure having the shape of the die and heat treating the structure into a coping conforming in shape to the die.

11 Claims, 9 Drawing Sheets

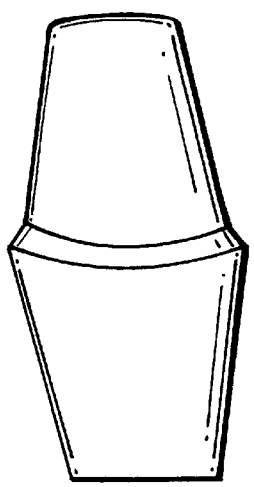
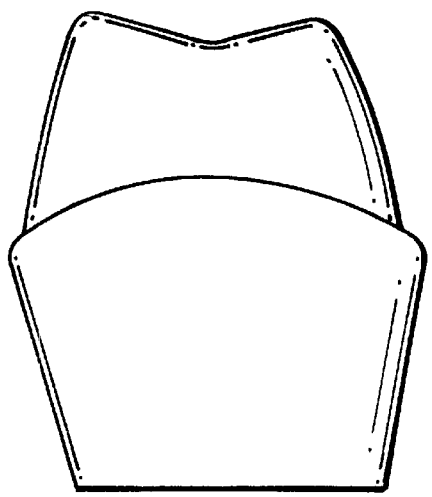
FIG. 2(a)  FIG. 2(b)
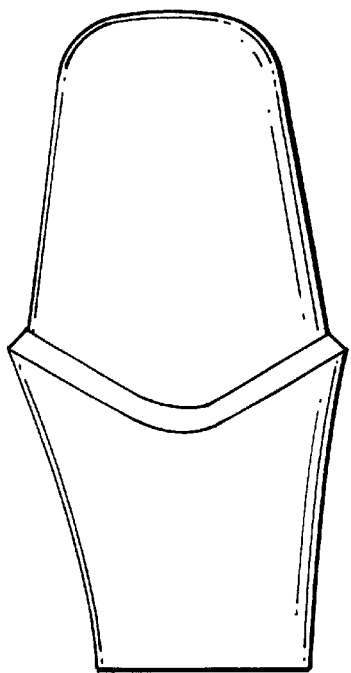
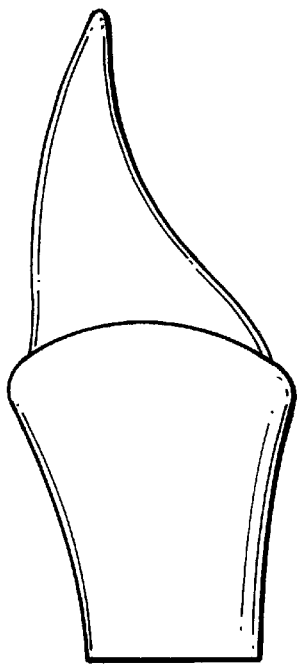
FIG. 3(a)  FIG. 3(b)

METHOD OF FORMING A DENTAL COPING

FIELD OF THE INVENTION

This invention relates to a method of forming a dental coping for use in the preparation of a dental restoration.

BACKGROUND OF THE INVENTION

A metal coping is used in dentistry in the construction of a dental crown and/or a bridge. The metal coping functions as the under structure of the crown and is usually covered, for reasons of aesthetics, with a fired-on coating of a ceramic porcelain composition or a polymer based veneering material. The metal coping supports the coating and provides the required structural strength and rigidity for the restored tooth to resist the forces of mastication.

A metal coping may be cast from an investment of a wax or plastic pattern of the tooth to be restored. An alternative procedure for forming a precious metal coping which does not require waxing, investing or casting has currently been gaining wide acceptance in the dental profession by both dentists and dental laboratories. This alternative procedure requires the use of a moldable material composition formed from a base material composed of a mixture of high and low fusing temperature metal particles and a binder preferably of dental wax as is disclosed, for example, in U.S. Pat. Nos.: 5,234,343, 5,593,305 and 5,730,600 respectively, each disclosure of which is herein incorporated by reference. The dental material is molded over a die into the shape of the tooth to be restored and heat treated at an elevated temperature above the melting temperature of the low fusing temperature metal particles and below the melting temperature of the high fusing temperature metal particles. Heat treatment transforms the molded structure into a porous metallic shell having the same shape as before heat treatment without suffering any significant shrinkage. The dental wax in the molded material vaporizes during heat treatment leaving the porous metallic shell with a high void volume of preferably above at least 20%. A filler material of metal or ceramic is melted into the porous shell to densify and solidify the shell into a dental coping having the identical shape of the die and in the tooth preparation as prepared by the dentist or dental laboratory. The filler material may be added either in a secondary heat treatment operation or during the primary heat treatment of the dental material.

The base material of high and low fusing temperature metal particles and wax binder may be configured into any geometrical shape for use by the dental laboratory such as, for example, in the form of a thin compacted strip of rectangular geometry. Likewise the filler material which is preferably of a precious metal such as gold or a gold alloy and wax binder may be configured into any geometrical shape preferably corresponding to the shape of the base material.

The method currently employed to form a coping from separate strips of base material and filler material is a labor intensive hand molding procedure in which the base material is cut into pieces each of which is applied by hand to the die. Thereafter the base material is adapted to the die by hand alone or in combination with a hand burnishing tool. An automated mechanism may also be used to adapt the base and filler materials to the die and to mold them over the die. These steps to adapt and mold the material to the die may be accomplished with the help of air pressure, water pressure, mechanical pressure or vacuum. The molded structure of base material is then heat treated to transform the molded structure into a porous metallic shell. Filler material is then melted into the porous shell in a heat treatment operation which may be performed independent of the heat treatment of the base material or alternatively by heat treating both the base and filler materials sequentially in a single heat treatment operation.

The hand molding operation is time consuming and labor intensive. Since the base material is a composition of precious metals and/or alloys the adaptation procedure is carried out in a way to minimize the loss of base material into waste. Moreover, once the base material is placed into contact against the die it may be contaminated and, if so, cannot be readily recycled.

SUMMARY OF THE INVENTION

An automated method has been discovered in accordance with the present invention to form a dental coping from a sheet of metallic material and preferably from a first sheet of a base composition of high and low fusing temperature metal particles and a binder and a second sheet of a filler material or a laminate of a base material and filler material with the method resulting in reducing the need for human intervention. The first and second sheets of material may be placed on top of one another to form an single sheet of two layers and/or the base and filler may themselves be represented by multiple layers. The filler material should be of precious metal or ceramic and the base material composition should preferably be relatively soft and malleable and of metal(s) or metal alloys which are compatible for use by the dental profession to restore teeth. The base material and filler material composition taught in the aforementioned patents are the preferred materials.

The automated method of the present invention for forming a dental coping comprises: scanning a three dimensional image of the die of the tooth or teeth to be restored; digitizing the scanned three dimensional image into digital information, storing the digital information in a computer; feeding the digital information from the computer into a computerized numerical control cutting machine; cutting out a section of material of metallic composition into a two dimensional configuration representing a two dimensional lay out of the scanned three dimensional image, adapting the cut out section of material over the die so that the material covers the die surface in close engagement therewith to form a single three dimensional structure having the shape of the die and heat treating the structure into a coping conforming in shape to the die.

In accordance with the present invention when two separate sheets of base and filler material are used a section of each sheet is cut out to form a two dimensional lay out of of the scanned three dimensional image of the die with the cut out section of filler material placed over the molded structure of base material before or after heat treatment. The cut out section of filler material should be equal or different in dimension so that the surface area of the cut out section will fill the porous structure of base material after heat treatment leaving slightly less filler material around the rim which forms the margin.

In a preferred alternative embodiment of the method of the present invention the die of the tooth or teeth to be restored may be formed having at least one reference marker such that the two dimensional lay out of base material will have a complementary reference marker to assist in providing a starting location or for establishing alignment when wrapping the cut out section of base material over the die. In this way the reference marker may be used to facilitate the adaptation of the two dimensional cut out section to the die. An additional reference marker may be formed in the two dimensional cut out section either manually or automatically to provide accuracy during placement and proper alignment in the adaptation of the cut out section of base material to the die.

BRIEF DESCRIPTION OF THE DRAWINGS

Additional advantages of the present invention will become apparent from the following detailed description of the invention when read in conjunction with the accompanying drawings of which:

FIG. 2(a) is a typical die configuration for a prepared premolar tooth shown from the buccal side of the tooth;

FIG. 2(b) is a similar view of the prepared die for the premolar tooth of FIG. 2(a) shown from the distall or mesial side of the tooth;

FIG. 3(a) is a typical die configuration for a prepared central tooth shown from the buccal side of the tooth;

FIG. 3(b) is a similar view of the prepared die for the central tooth of FIG. 3(a) shown from the distal or mesial side of the tooth;

DETAILED DESCRIPTION OF THE INVENTION

Figure 1:
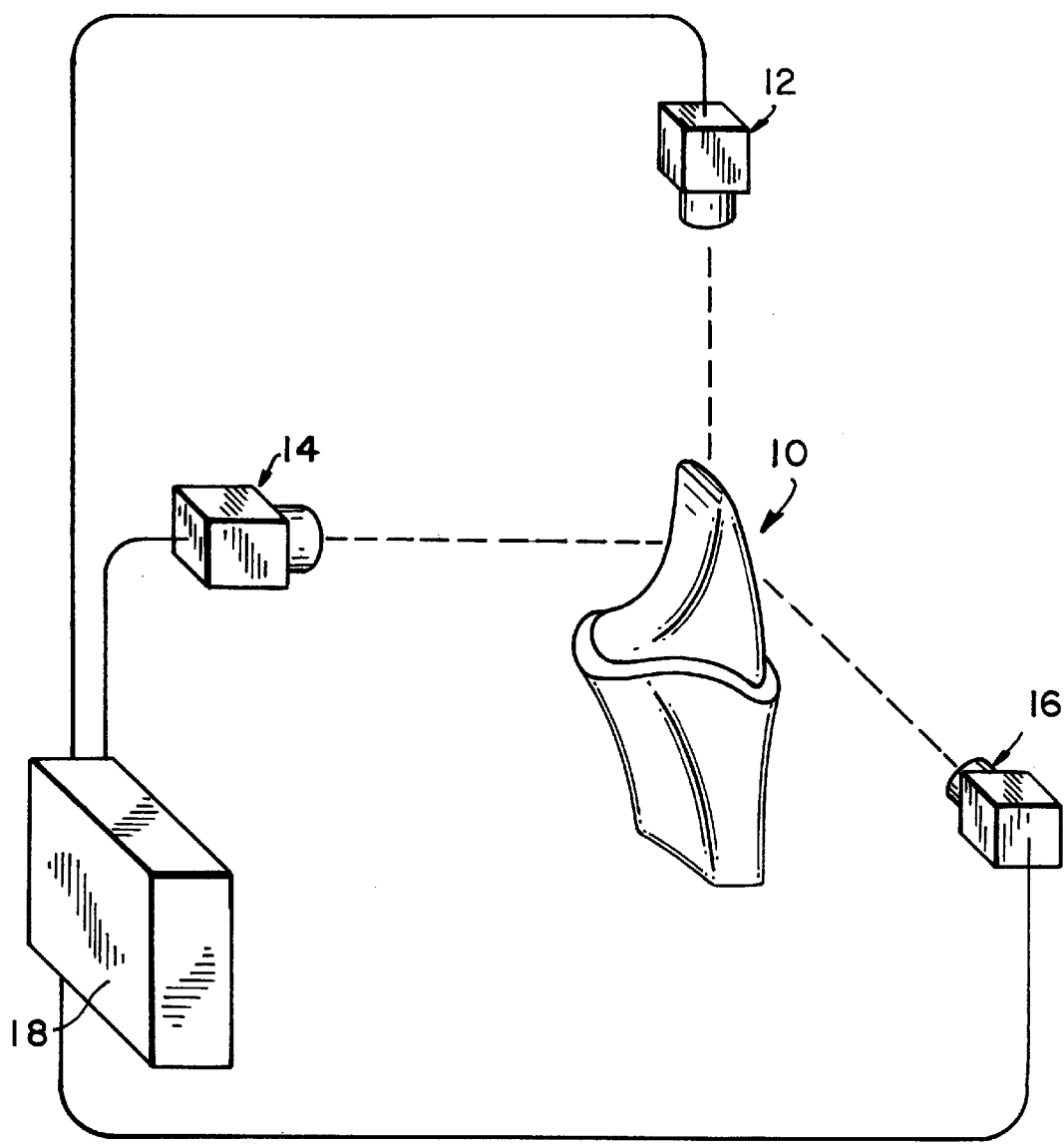
FIG. 1 is a schematic diagram of an arrangement for scanning a three dimensional image of a die prepared from an impression of a tooth for forming a coping in accordance with the present invention.
Figure 4A:
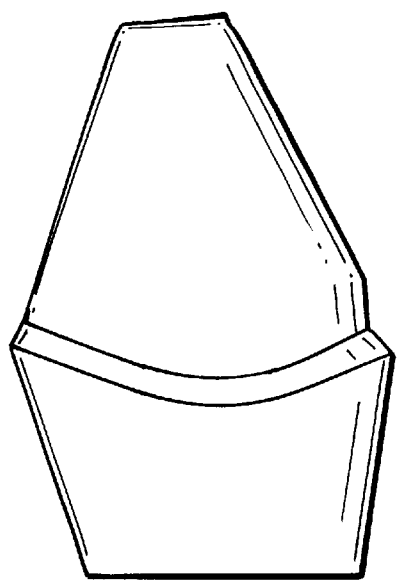
FIG. 4(a) is a typical die configuration for a prepared canine tooth shown from the buccal side of the tooth.
Figure 4B:
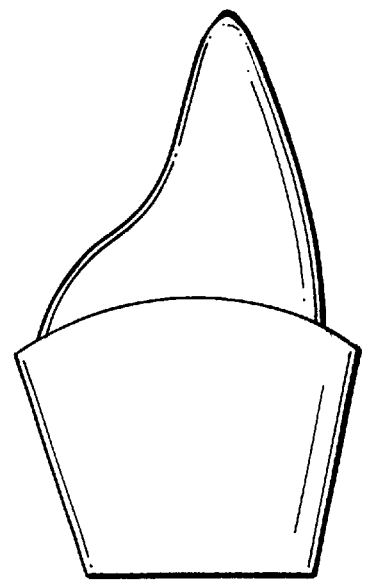
FIG. 4(b) is a similar view of the prepared die for the canine tooth of FIG. 4(a) shown from the distal or mesial side of the tooth.
Figure 5A:
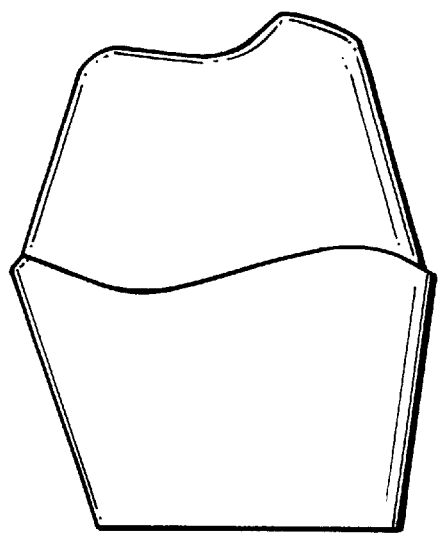
FIG. 5(a) is a typical die configuration for a prepared molar tooth shown from the buccal side of the tooth.
Figure 5B:
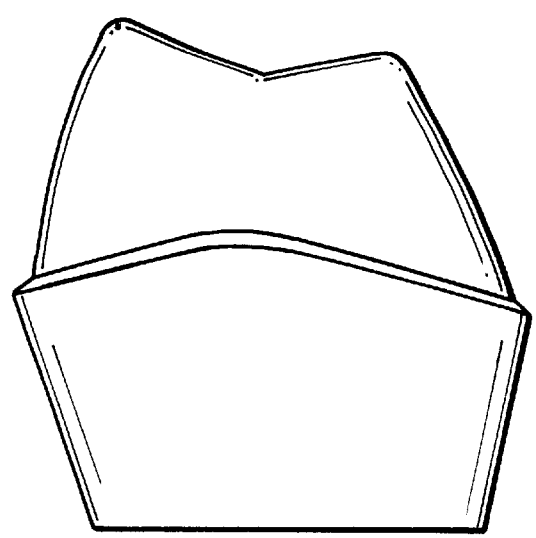
FIG. 5(b) is a similar view of the prepared die for the molar tooth of FIG. 5(a) shown from the distal or mesial side of the tooth.

A schematic diagram of a preferred arrangement for scanning a three dimensional image of a stone or refractory die 10 prepared from an impression of a tooth to be restored is shown in FIG. 1. The die 10 is positioned in juxtaposition relative to three CCD cameras or diode lasers 12, 14 and 16 and is spatially separated 90° or more apart from one another along three coordinate axes x, y and z respectively so that the cameras or lasers 12, 14 and 16 face opposite surfaces surrounding the die 10. The diode lasers 12, 14 and 16 are moved relative to the die 10 or vice versa to scan the surface of the die 10 on all sides thereof to generate coordinate data representative of the three dimensional image of the die. The coordinate data corresponding to the three dimensional image of the die 10 is stored in digital form in the memory of a computer 18. As an alternative to the arrangement shown in FIG. 1 a single laser beam may be arranged in a plane lying preferably at an angle such as 45° to the die while the die is rotated a complete 360°. The latter is equivalent to the operation of an electromechanical stylus placed in physical contact with the die as the die is rotated. Another alternative is to form a shadow of the die by a projection from a light source and to scan the projection while rotating the die. It is to be understood that many alternatives are conventionally known to form a three dimensional image of an object such as a die and to convert the coordinates into digital information. Moreover, although FIG. 1 shows the use of three cameras or three lasers it is to be understood the subject invention is not limited to any specific number of cameras or lasers and that an electromechanical scanning device may equally be used. Moreover any conventional method may be used to scan the die to form a three dimensional image and any conventional method may be used for converting the three dimensional image into digital data for storage in a computer.

In accordance with the present invention the digital data corresponding to the three dimensional image of the die 10 is used to form a two dimensional rendering of the surface topography of the die 10 hereafter referred to as a two dimensional lay out which is automatically cut out from a sheet of material using a conventional computer controlled CC mill or conventional CC lathe (not shown) or other such conventional computer controlled cutting device hereafter referred to as a numerical controlled cutting machine.

The material used to form a cut out of the three dimensional image may be a single sheet of dental material representing a laminate of a base material and filler material as taught earlier or may be cut out from separate sheets of base and filler material as taught in the aforementioned patents. The base and filler materials may each be divided into two or more layers to form multilayers of the base and filler materials. The preferred base material is composed of high and low fusing temperature metal particles selected from one or more metal or metal alloys, preferably of precious metals such as platinum and palladium in any desired proportion relative to one another from zero to one hundred percent in addition to a binder preferably of wax. Additional constituents may be added such as gold, silver, copper, magnesium, aluminum, zinc, gallium, indium and other metals selected from the third, fourth or fifth group of elements of the periodic table. The total weight percent of the metallic elements other than gold, silver, and the platinum group metals should not exceed ten percent. The filler material is composed primarily or entirely of low fusing temperature metal particles preferably of gold or a gold alloy and the wax binder may vary widely although preferably between about twenty percent by volume and up to eighty percent by volume of the base material composition. Any wax may be used which is relatively soft and tacky to form the binder and may be selected from any natural wax, mineral wax, or organic wax composition.

As indicated above the base and filler materials may constitute separate sheets of material or a dual laminate. When two sheets are used a cut out of each is formed in accordance with the present invention with the cut out of filler metal placed over the cut out of base material after the base material cut out is heat treated or before it is heat treated. In the latter case both may be heat treated in sequence in a dental furnace. When the base and filler material are separate sheets the cut out sections may be identical in dimension or different in dimension. When a dual sheet of base and filler material is used only one cut out is necessary.

The coordinate data corresponding to the three dimensional image of the die 10 is fed from the computer 18 to the numerical controlled cutting machine (not shown) for performing a conventional CAD-CAM routine so that the numerical controlled cutting machine will cut out a section from a thin sheet of material having a geometry with a surface area resulting in a two-dimensional rendering of the topography of the die 10.

Figure 6A:
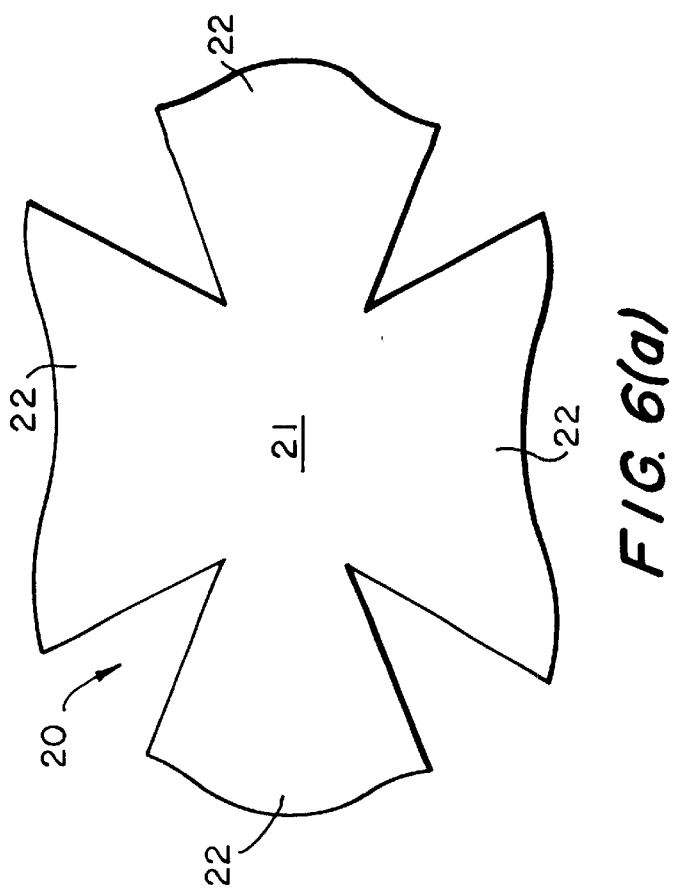
FIG. 6(a) is a plan view of a two dimensional layout of the surface configuration for a typical premolar tooth in accordance with the present invention.
Figure 6B:
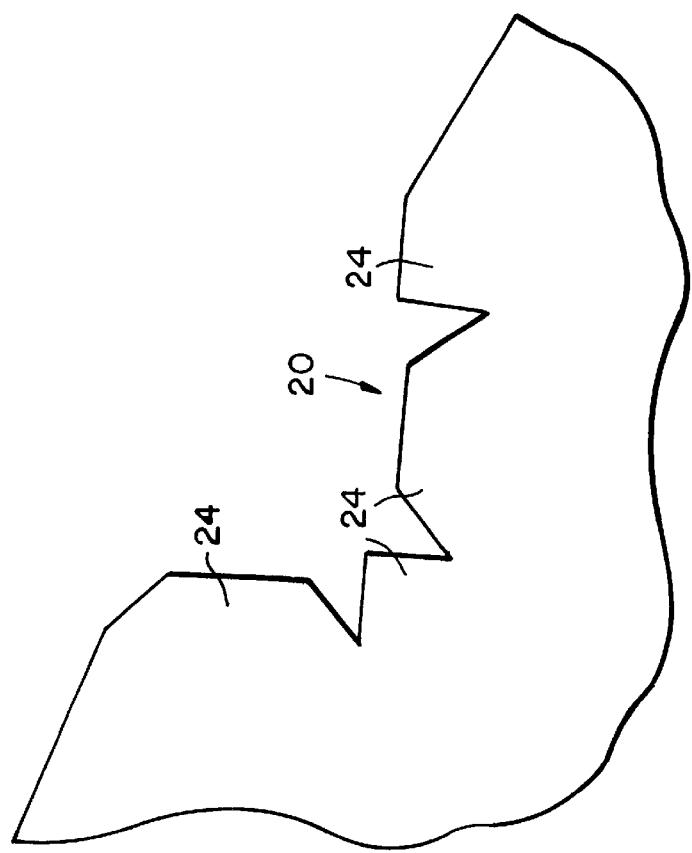
FIG. 6(b) is plan view of another two dimensional layout of the surface configuration for a typical premolar tooth in accordance with the present invention.
Figure 6C:
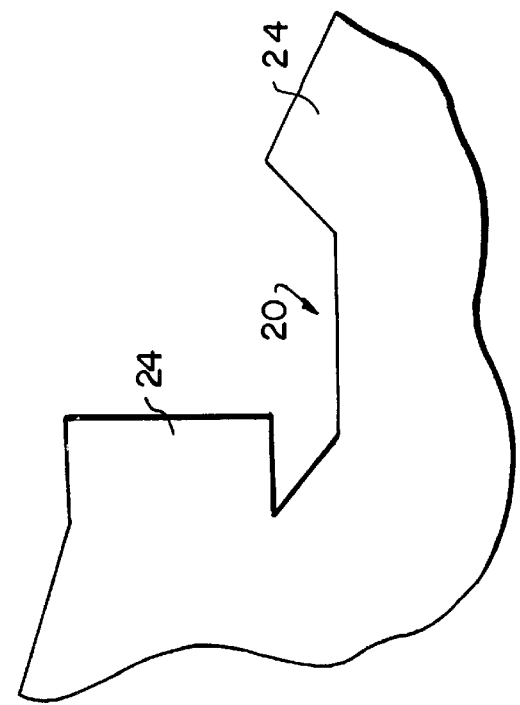
FIG. 6(c) is yet another plan view of another two dimensional layout of the surface configuration for a typical premolar tooth in accordance with the present invention.

Typical die configurations for different typical tooth preparations for a premolar, central, canine and molar tooth is shown in FIGS. 2–5 respectively with FIGS. 6–9 representing a plan view of different two-dimensional renderings of the surface configuration corresponding to the different die configurations of FIGS. 2–5. Each plan view shows a cut out section which is cut out by the numerically controlled cutting machine from the base and filler materials respectively. Accordingly, FIG. 6(*a*) shows one configuration of a cut out section 20 representing a two dimensional layout of the surface configuration for a typical premolar tooth which is intended to be adapted to the die 10 by placing the center 21 of the cut out section 20 over the occlusal surface of the die and folding back the flap portions 22. Alternatively, the cut out section 20 for the same premolar tooth of FIG. 6(*a*) may be configured as shown in FIGS. 6(*b*) and 6(*c*) so that the cut out section 20 may be wrapped about the circumference of the die 10 before folding over the cut out section flaps 23 or 24 over the occlusal surface of the die 10.

The configuration of the cut out section 20 will depend on the surface geometry of the tooth preparation which is determined by the dentist before the die 10 of the tooth is taken. The configuration which will result in causing the least number of seams needed to adapt the cut out section 20 to the die 10 and with minimal pleats is preferred. The selection of the configuration can be determined by mathematical calculation and/or after repeated experimentation and experience and written into the software for controlling the numerical cutting machine.

Figure 7B:
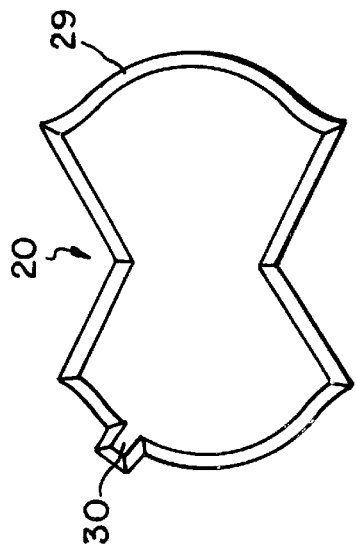
FIG. 7(b) is a view similar to that of FIG. 7(a) showing the two dimensional layout with its outer edge beveled and showing a reference projection in accordance with the present invention.
Figure 7A:
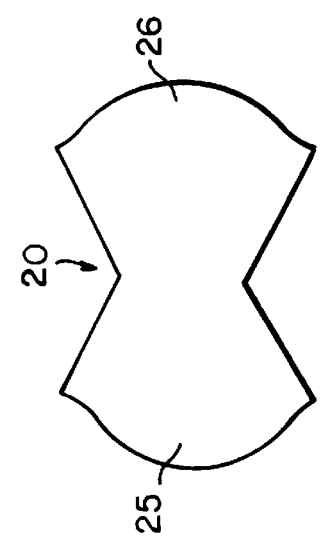
FIG. 7(a) is a plan view of a two dimensional layout of the surface configuration for a typical central tooth in accordance with the present invention.
Figure 7C:
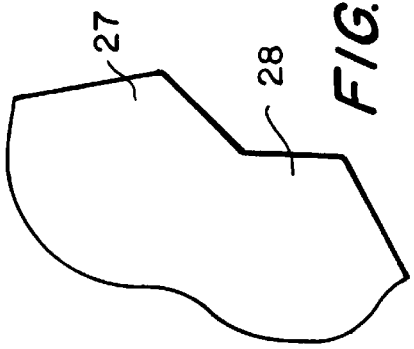
FIG. 7(c) is plan view of another two dimensional layout of the surface configuration for a typical central tooth in accordance with the present invention.
Figure 8A:
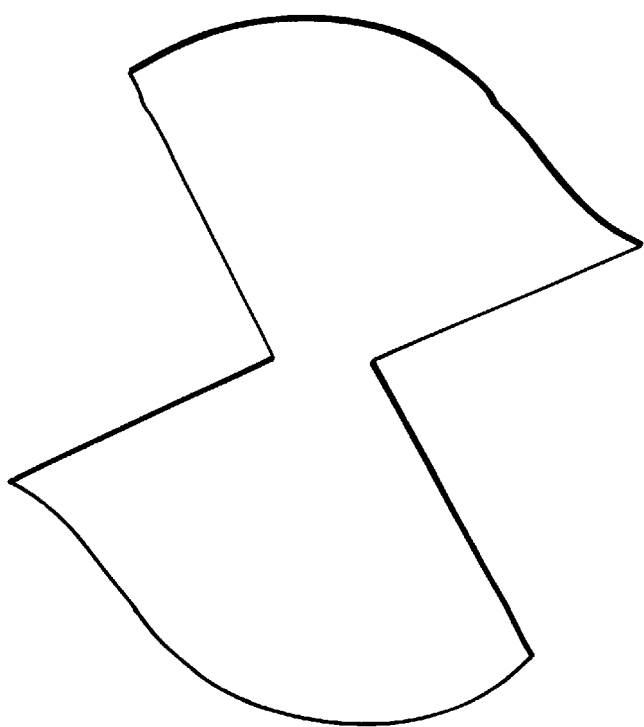
FIG. 8(a) is a plan view of a two dimensional layout of the surface configuration for a typical canine tooth in accordance with the present invention.
Figure 8B:
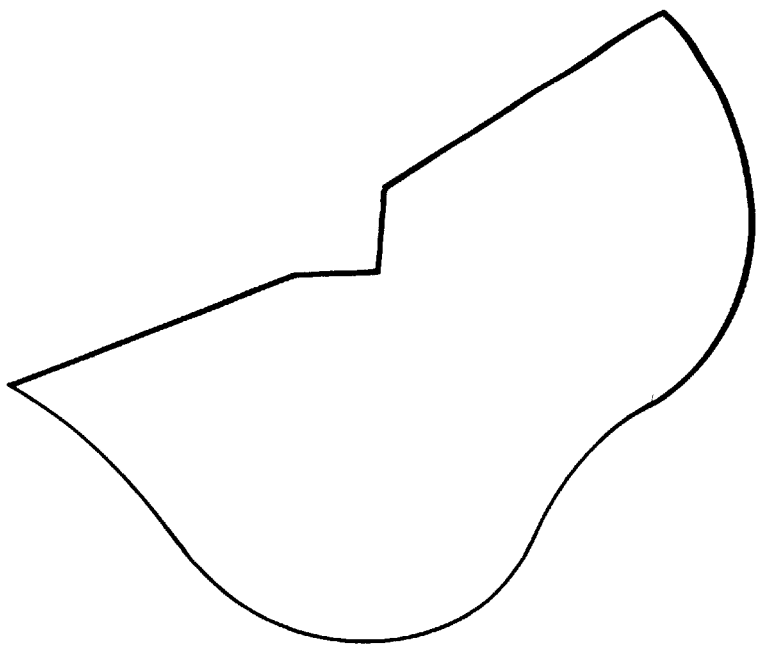
FIG. 8(b) is plan view of another two dimensional layout of the surface configuration for a typical canine tooth in accordance with the present invention.
Figure 9B:
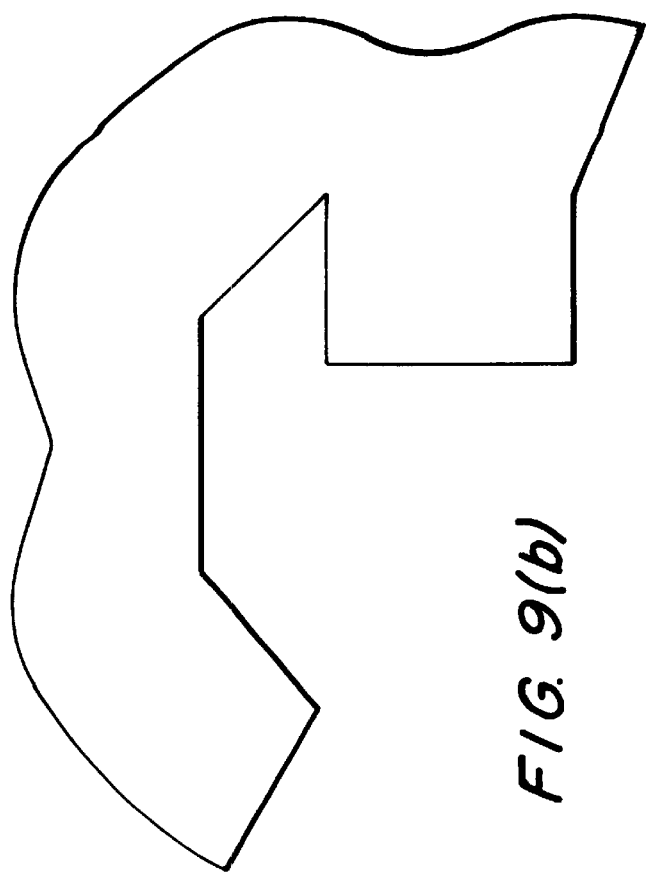
FIG. 9(b) is a plan view of another two dimensional layout of the surface configuration for a typical molar tooth in accordance with the present invention.
Figure 9A:
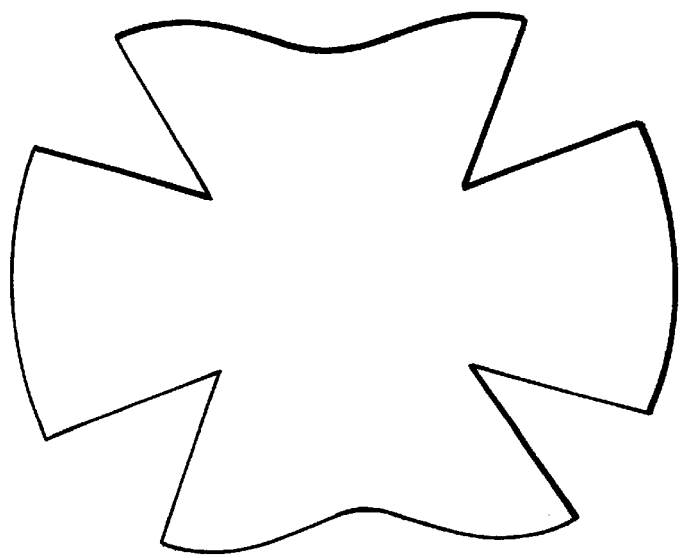
FIG. 9(a) is a plan view of a two dimensional layout of the surface configuration for a typical molar tooth in accordance with the present invention.
Figure 9C:
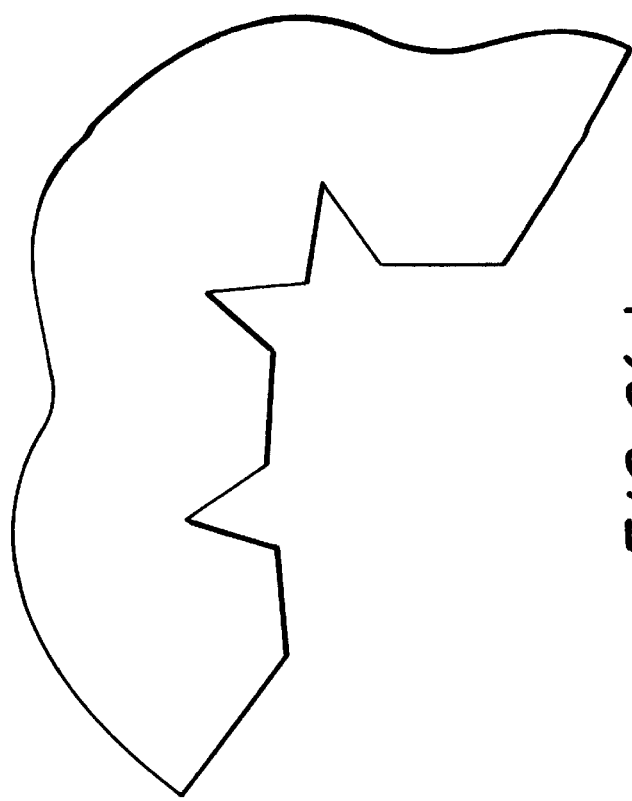
FIG. 9(c) is yet another plan view of a two dimensional layout of the surface configuration for a typical canine tooth in accordance with the present invention.
Figure 9D:
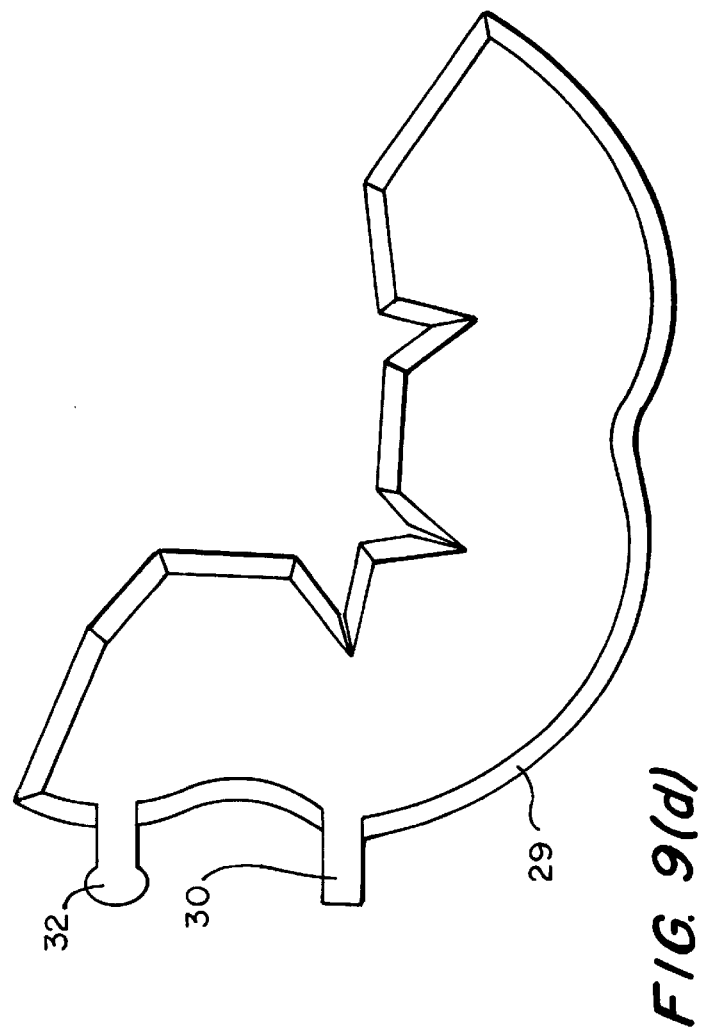
FIG. 9(d) is a view substantially similar to that of FIG. 9(c) showing the two dimensional layout with its outer edge beveled and showing two reference projections in accordance with the present invention.

The cut out sections 20 of FIGS. 7, 8 and 9 are plan views for a typical central, canine and molar tooth respectively and although of different shape and surface configuration from that of FIG. 6 they all represent two-dimensional renderings in accordance with the present invention of the surface configuration corresponding to the different die configurations. Once again the cut out section 20 may be configured to form sectors 25 and 26 which as shown in FIG. 7(*a*) will readily fold over the occlusal surface of the die 10 or wrapped as one section about the circumference of the die 10 as shown in FIG. 7(*c*) with the cut out section 20 having flaps 27 and 28 which fold over the occlusal surface of the die 10.

A cut out section 20 may be cut out to form a beveled edge 29 around the outer rim as shown in FIG. 7(*b*). Moreover, the die 10 may be formed with a reference/alignment marker (not shown) to identify the proper placement for the cut out section 20 when adapting it to the die 10. The reference/alignment marker (not shown) can be of any shape and in any form representing, for example, a slit or groove located on the die 10 preferably at a position extending from the margin of the die 10. When the die 10 is formed with a reference marker the cut out section 20 will automatically form a corresponding marker 30 which may appear as a projection extending from the cut out section 20. The marker 30 may also be used for alignment. However to provide both reference and alignment two markers 30 and 32 are preferred with the different markers having different shapes as shown in FIG. 9(*d*). In this way no error can be made in alignment particularly if the cut out section 20 is adapted to the die 10 by use of a robot.

Figure 10A:
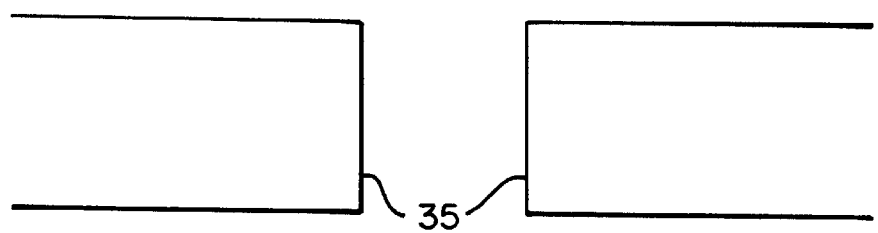
FIGS. 10(a), (b) and (c) show a number of different configurations for the mating ends of the cut out sections so as to form seams either in an abutting relationship as in FIG. 10(a) or in an overlapping relationship as in FIGS. 10(b) and 10(c) respectively.
Figure 10B:
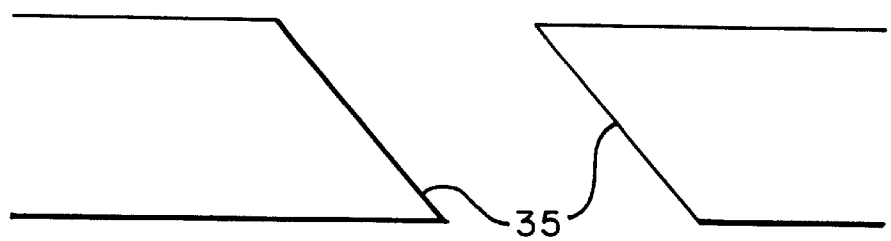
Figure 10C:
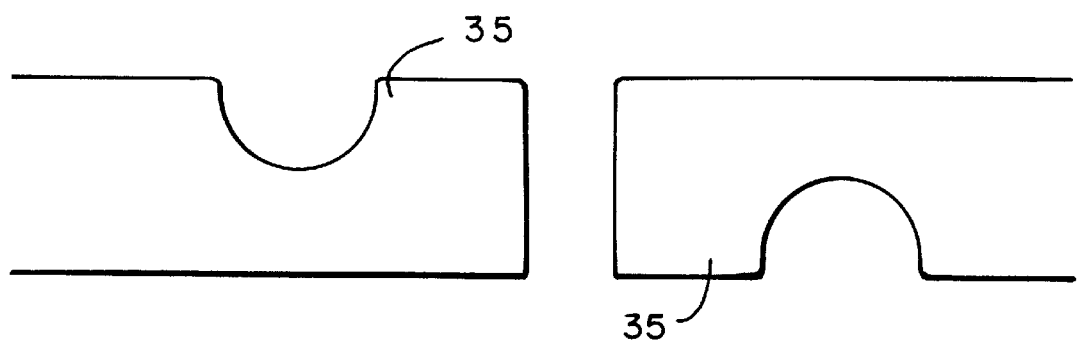

The two dimensional cut out section(s) 20 of all of the different configurations shown in FIGS. 2–9 have mating ends 35 which form one or more seams when the cut out section 20 is placed or wrapped over the die 10. The seams are formed by abutting the mating ends 35 together as shown in FIG. 10(*a*). In many instances an overlap of the mating ends is preferred and the thickness of the seam formed at the overlapping mating ends may be reduced by mechanical or automatic means. To minimize the thickness formed by an overlapping seam the mating ends 35 can be beveled as shown in FIG. 10(*b*) or otherwise contoured as for example as shown in FIG. 10(*c*) to form an interlock at the mating ends 35. Where the tooth preparation results in a cut out section 20 having a complicated surface configuration and/or where many seams will be necessary the mating ends 35 should be beveled to accommodate an overlap. Moreover, by overlapping the mating ends 35 the thickness of the seam can be controlled. The mating ends 35 may abut one another in which case there is no difference in thickness at the abutting seam.

To control the formation of seams at the mating ends 35 and to control the thickness of the seams a burnishing tool may be used. The burnishing tool may be applied after placement of the cut out section 20 over the die. Alternatively, the thickness can be smoothed out with the use of fingers or a swedger may be used. The burnishing tool or hand may be used in conjunction with the application of hot air and/or vacuum. One edge of the seam may be beveled with the mating edge placed over it and unified using a mechical burnisher.

The cut out section of base material may be more easily fitted over the die by applying heat to the cut out section.

Heat may be applied from a hot air applicator or from a lamp or from any other applicator which will provide a source of heat at a temperature within a temperature range of e.g. 25° C.–60° C. sufficent to soften the cut out section and render more pliable and tacky without causing it to become too soft and limp. In this way the warmed cut out section will easily adapt to the geometry of the die and will simplify any reduction in seam thickness, if necessary. Thereafter the molded cut out section is allowed to reharden upon the die. The molded cut out section can be removed from the die, particularly if hard waxes were used in the base composition, and heat treated as a self supporting structure at an elevated temperature for forming a coping or for forming a porous shell depending upon whether the cut out section is a dual layer of base and filler material or only a base material. Alternatively the cut out section may be heat treated on a refractory die. If the cut out section is composed only of base material a cut out of filler material may also be formed from the three dimensional information of the die and adapted to the die over the base cut out. Alternatively, the cut out of base material after it is heat treated can be dipped into a molten filler material bath.

What is claimed:

1. An automated method for forming a dental coping comprising the steps of: scanning a three dimensional image of the die of the tooth or teeth to be restored; digitizing the scanned three dimensional image into digital information, storing the digital information in a computer; feeding the digital information from the computer into a computerized numerical cutting machine; cutting out a section of material of metallic composition into a two dimensional configuration representing a two dimensional lay out of the scanned three dimensional image, adapting the cut out section of material over the die so that the cut out section covers the die surface in close engagement therewith to form a single three dimensional structure having the shape of the die and heat treating the structure into a coping conforming in shape to the die.

2. An automated method for forming a dental coping as defined in claim 1 wherein the cut out section of material is composed of a base material comprising high and low fusing temperature metal particles selected from one or more precious metals or precious metal alloys and a binder.

3. An automated method for forming a dental coping as defined in claim 2 wherein said binder is a wax.

4. An automated method for forming a dental coping as defined in claim 3 wherein the cut out section of material is a dual layer with one layer composed of a base material comprising high fusing temperature metal particles and with the other layer composed of a filler material of a precious metal of predominantly or exclusively of gold.

5. An automated method for forming a dental coping as defined in claim 3 wherein the cut out section is composed of a mutilayer base material and/or a multilayer filler material.

6. An automated method for forming a dental coping as defined in claim 1 wherein said two dimensional cut out section has at least one reference marker.

7. An automated method for forming a dental coping as defined in claim 6 wherein said two dimensional cut out section has two reference markers.

8. An automated method for forming a dental coping as defined in claim 7 wherein each of said reference markers is of different geometry.

9. An automated method for forming a dental coping as defined in claim 1 wherein said cut out section has beveled edges.

10. An automated method for forming a dental coping as defined in claim 1 wherein the cut out section is heat treated to soften it before being fitted over the die.

11. An automated method for forming a dental coping as defined in claim 10 wherein the softened cut out section is allowed to reharden and is then removed from the die before being heat treated at an elevated temperature.

* * * * *